United States Patent [19]

Namiki et al.

[11] Patent Number: 5,448,498
[45] Date of Patent: Sep. 5, 1995

[54] APPARATUS FOR GENERATING A CONSTRAINT CONDITION IN A MOLECULAR DYNAMICS SIMULATION

[75] Inventors: Takefumi Namiki; Ikuo Fukuda; Munetaka Takeuchi; Masuhiro Mikami; Kota Sakai, all of Kawasaki, Japan

[73] Assignee: Fujitsu Limited, Kawasaki, Japan

[21] Appl. No.: 982,715

[22] Filed: Nov. 27, 1992

[30] Foreign Application Priority Data

Nov. 26, 1991 [JP] Japan ................................. 3-310606

[51] Int. Cl.$^6$ ............................................. G06F 17/50
[52] U.S. Cl. ................................... 364/496; 364/578
[58] Field of Search ........... 364/496, 499, 578, 413.13, 364/413.15; 436/86, 89; 935/87; 395/100, 119, 920, 932

[56] References Cited

U.S. PATENT DOCUMENTS 5,241,470  8/1993  Lee et al. ............................ 364/499
5,260,882  11/1993  Blanco et al. ....................... 364/499

FOREIGN PATENT DOCUMENTS 9104543  4/0491  WIPO .

OTHER PUBLICATIONS

IBM Systems Journal, vol. 28, No. 4, 1989, Armonk, N.Y. "Designing Molecules and Crystals by Computer", A. Koide, pp. 613–627.
Witten; "Computation Medicine, Frankenstein in the Machines"; IEEE 1991.
Weiner; "Parallel Processing and Computational Chemistry. " IEEE 1989.

*Primary Examiner*—Ellis B. Ramirez
*Attorney, Agent, or Firm*—Staas & Halsey

[57] ABSTRACT

A constraint condition generating apparatus generates a constraint condition which should be output to a molecular dynamics simulator for simulating a behavior of a molecule based on a molecular dynamics method under the constraint condition for freezing a part of the degree of freedom within the molecule. This apparatus comprises bond constraint condition setting and releasing unit for setting a bond constraint list comprising the number of two atoms whose bond are to be constrained and a bonding distance between two atoms, and for releasing the constraint of the bond of two atoms, angle constraint condition setting and releasing means for setting an angle constraint condition including a bonding distance between two atoms which are not common and for releasing a part of angle constraint condition in accordance with a designation by a user; and a torsion constraint condition setting and releasing unit for setting a torsion constraint condition including a bonding distance between two atoms which are not common, and for releasing a part of a constraint condition in accordance with a designation by a user.

10 Claims, 21 Drawing Sheets

BOND (BONDING DISTANCE)

ANGLE (BONDING ANGLE, CENTRAL ANGLE)

TORSION (DIHEDRAL, ANGLE BETWEEN PLANES)

CHEMICAL STRUCTURE FORMULA
OF ACETIC ACID

| NUMBER (I) | NUMBER (J) | BOND |
|---|---|---|
| 1 | 4 | 1.4 |
| 2 | 4 | 1.4 |
| 3 | 4 | 1.4 |
| 4 | 5 | 1.53 |
| 5 | 6 | 1.2 |
| 5 | 7 | 1.33 |
| 7 | 8 | 0.95 |

BOND CONSTRAINT LIST

FIG. 4A

| NUMBER (I) | NUMBER (J) | NUMBER (K) | ANGLE |
|---|---|---|---|
| 1 | 4 | 2 | 109.4 |
| 1 | 4 | 3 | 109.4 |
| 1 | 4 | 5 | 109.4 |
| 2 | 4 | 3 | 109.4 |
| 2 | 4 | 5 | 109.4 |
| 3 | 4 | 5 | 109.4 |
| 4 | 5 | 6 | 120 |
| 4 | 5 | 7 | 120 |
| 6 | 5 | 7 | 120 |
| 5 | 7 | 8 | 109.4 |

ANGLE CONSTRAINT LIST

FIG. 4B

| NUMBER (I) | NUMBER (J) | NUMBER (K) | NUMBER (L) | TORSION |
|---|---|---|---|---|
| 4 | 1 | 5 | 6 | 90 |
| 4 | 1 | 5 | 7 | 90 |
| 4 | 2 | 5 | 6 | 30 |
| 4 | 2 | 5 | 7 | 30 |
| 4 | 3 | 5 | 6 | 150 |
| 4 | 3 | 5 | 7 | 150 |
| 5 | 4 | 7 | 8 | 180 |
| 5 | 6 | 7 | 8 | 180 |

TORSION CONSTRAINT LIST

| NUMBER (I) | NUMBER (J) | BOND |
|---|---|---|
| 4 | 5 | 1.53 |
| 5 | 7 | 1.33 |
| 7 | 8 | 0.95 |

BOND CONSTRAINT LIST

| NUMBER (I) | NUMBER (J) | NUMBER (K) | ANGLE |
|---|---|---|---|
| 4 | 5 | 7 | 120 |
| 5 | 7 | 8 | 109.4 |

ANGLE CONSTRAINT LIST

| NUMBER (I) | NUMBER (J) | NUMBER (K) | NUMBER (L) | TORSION |
|---|---|---|---|---|
| 5 | 4 | 7 | 8 | 180 |

TORSION CONSTRAINT LIST

| NUMBER (I) | NUMBER (J) | BOND |
|---|---|---|
| 5 | 7 | 1.33 |
| 7 | 8 | 0.95 |

BOND CONSTRAINT LIST

| NUMBER (I) | NUMBER (J) | NUMBER (K) | ANGLE |
|---|---|---|---|
| 5 | 7 | 8 | 109.4 |

ANGLE CONSTRAINT LIST

| NUMBER (I) | NUMBER (J) | BOND |
|---|---|---|
| 5 | 7 | 1.33 |

← CONSTRAINT ONLY BOND (5-7)

BOND CONSTRAINT LIST

FIG. 7A

| BOND POTENTIAL FUNCTION | $E(l) = K_B(l - l_0)^2$ |
|---|---|

FIG. 7B

| NUMBER (I) | NUMBER (J) | PARAMETER $l_0$ | PARAMETER K |
|---|---|---|---|
| 1 | 4 | 1.4 | 3.2 |
| 2 | 4 | 1.4 | 3.2 |
| 3 | 4 | 1.4 | 3.2 |
| 4 | 5 | 1.53 | 4.3 |
| 5 | 6 | 1.2 | 6.1 |
| 5 | 7 | 1.33 | 5.5 |
| 7 | 8 | 0.95 | 3.5 |

BOND POTENTIAL PARAMETER

FIG. 7C

| ANGLE POTENTIAL FUNCTION | $E(\theta) = K_A(\theta - \theta_0)^2$ |
|---|---|

FIG. 7D

| NUMBER (I) | NUMBER (J) | NUMBER (K) | PARAMETER $\theta_0$ | PARAMETER K |
|---|---|---|---|---|
| 1 | 4 | 2 | 109.4 | 10.2 |
| 1 | 4 | 3 | 109.4 | 10.2 |
| 1 | 4 | 5 | 109.4 | 9.8 |
| 2 | 4 | 3 | 109.4 | 10.2 |
| 2 | 4 | 5 | 109.4 | 9.8 |
| 3 | 4 | 5 | 109.4 | 9.8 |
| 4 | 5 | 6 | 120 | 12.4 |
| 4 | 5 | 7 | 120 | 11.6 |
| 6 | 5 | 7 | 120 | 13.0 |
| 5 | 7 | 8 | 109.4 | 10.3 |

ANGLE POTENTIAL PARAMETER

FIG. 8A

| TORSION POTENTIAL COEFFICIENT | $E(\phi) = K_T [1 + \cos(\phi + \phi_0)]$ |
|---|---|

FIG. 8B

| NUMBER (I) | NUMBER (J) | NUMBER (K) | NUMBER (L) | PARAMETER $\phi_0$ | PARAMETER $K_T$ |
|---|---|---|---|---|---|
| 4 | 1 | 5 | 6 | 90  | 5.7 |
| 4 | 1 | 5 | 7 | 90  | 5.5 |
| 4 | 2 | 5 | 6 | 30  | 5.7 |
| 4 | 2 | 5 | 7 | 30  | 5.5 |
| 4 | 3 | 5 | 6 | 150 | 5.7 |
| 4 | 3 | 5 | 7 | 150 | 5.5 |
| 5 | 4 | 7 | 8 | 180 | 6.2 |
| 5 | 6 | 7 | 8 | 180 | 7.4 |

TORSION POTENTIAL PARAMETER

BOND

ANGLE

TORSION

CHEMICAL STRUCTURE FORMULA OF ACETIC ACID

| SERIAL NUMBER OF ATOMS | ELEMENT SYMBOL | X COORDINATE | Y COORDINATE | Z COORDINATE |
|---|---|---|---|---|
| 1 | H | -0.7 | 0.0 | 1.21 |
| 2 | H | -0.7 | 1.21 | -0.7 |
| 3 | H | -0.7 | -1.21 | -0.7 |
| 4 | C | 0.0 | 0.0 | 0.0 |
| 5 | C | 1.53 | 0.0 | 0.0 |
| 6 | O | 2.20 | 1.15 | 0.0 |
| 7 | O | 2.20 | -1.15 | 0.0 |
| 8 | H | 3.15 | -1.15 | 0.0 |

ATOMIC INFORMATION

| SERIAL NUMBER OF ATOM (1) | SERIAL NUMBER OF ATOM (2) |
|---|---|
| 1 | 4 |
| 2 | 4 |
| 3 | 4 |
| 4 | 5 |
| 5 | 6 |
| 5 | 7 |
| 7 | 8 |

BONDING LIST

FIG. 16A

| NUMBER (I) | NUMBER (J) | BONDING DISTANCE OF I AND J |
|---|---|---|
| 1 | 4 | 1.4 |
| 2 | 4 | 1.4 |
| 3 | 4 | 1.4 |
| 4 | 5 | 1.53 |
| 5 | 6 | 1.2 |
| 5 | 7 | 1.33 |
| 7 | 8 | 0.95 |

BOND

FIG. 16B

| NUMBER (I) | NUMBER (J) | NUMBER (K) | BONDING DISTANCE OF I AND J |
|---|---|---|---|
| 1 | 4 | 2 | 1.62 |
| 1 | 4 | 3 | 1.62 |
| 1 | 4 | 5 | 2.04 |
| 2 | 4 | 3 | 1.62 |
| 2 | 4 | 5 | 2.04 |
| 3 | 4 | 5 | 2.04 |
| 4 | 5 | 6 | 2.37 |
| 4 | 5 | 7 | 2.48 |
| 6 | 5 | 7 | 2.19 |
| 5 | 7 | 8 | 1.87 |

ANGLE

FIG. 16C

| NUMBER (I) | NUMBER (J) | NUMBER (K) | NUMBER (L) | BONDING DISTANCE OF I AND J |
|---|---|---|---|---|
| 4 | 1 | 5 | 6 | 3.28 |
| 4 | 1 | 5 | 7 | 3.76 |
| 4 | 2 | 5 | 6 | 3.28 |
| 4 | 2 | 5 | 7 | 3.76 |
| 4 | 3 | 5 | 6 | 3.28 |
| 4 | 3 | 5 | 7 | 3.76 |
| 5 | 4 | 7 | 8 | 3.95 |
| 5 | 6 | 7 | 8 | 3.82 |

TORSION

FIG. 19

|  | DONE | CANCEL |
|---|---|---|

BOND POTENTIAL LIST

| | BOND ID | FORCE CONSTANT | BOND LENGTH (Å) |
|---|---|---|---|
| ⇧ | 1 - 2 | 250.0000 | 1.5400 |
| | 2 - 3 | 250.0000 | 1.5400 |
| ⇩ | 3 - 4 | 250.0000 | 1.5400 |
| | 4 - 5 | 250.0000 | 1.5400 |

NUMBER OF BONDS = 79

ANGLE POTENTIAL LIST

| | ANGLES ID | F CONSTANT | BOND ANGLE (DEG) |
|---|---|---|---|
| ⇧ | 1 - 2 - 3 | 78.0000 | 109.500 |
| | 2 - 3 - 4 | 78.0000 | 109.500 |
| ⇩ | 3 - 4 - 5 | 78.0000 | 109.500 |
| | 4 - 5 - 6 | 78.0000 | 109.500 |

NUMBER OF ANGLES = 43

TORSION POTENTIAL LIST

| | TORSION ID | FORCE CONSTANT | CN |
|---|---|---|---|
| ⇧ | 1 - 2 - 3 - 4 | 2.00000 | -2.0000 |
| | 2 - 3 - 4 - 5 | 2.00000 | -2.0000 |
| ⇩ | 3 - 4 - 5 - 6 | 2.00000 | -2.0000 |
| | 4 - 5 - 6 - 7 | 2.00000 | -2.0000 |

NUMBER OF TORSIONS = 48

APPARATUS FOR GENERATING A CONSTRAINT CONDITION IN A MOLECULAR DYNAMICS SIMULATION

BACKGROUND OF THE INVENTION

1. Field of the Invention

The present invention relates to an apparatus for automatically generating a constraint condition of a molecule in a molecular dynamics method. The apparatus can be used in a device for simulating the behavior of a molecule using a computer, based on the molecular dynamics method, for the purpose of developing a new substance, for example.

2. Description of the Related Art

An application technology for a super-computer, for example, which is suitable for high-speed scientific and engineering computation, is a simulator utilizing the molecular dynamics method. The simulator receives the initial coordinates of an atom, the initial speed of an atom, a potential function between atoms, the mass of an atom, and the electric charge of an atom, for example, and simulates the behavior of a molecule based on the molecular dynamics method, thereby obtaining the properties of a substance.

A constraint condition for freezing or limiting some parts of the degrees of freedom within the molecule is provided as input information for the simulator. The molecular dynamics method is used in order to examine the effect of a predetermined force applied between the atoms when a simulation is performed by using the molecular dynamics method. In this case, technology for generating the constraint condition with accuracy and ease is required.

Before explaining the prior art of the apparatus for generating the constraint condition using the molecular dynamics method, a summary of the molecular dynamics method will be briefly given. The molecular dynamics method performs a computer simulation of a behavior of molecules by moving the particles using the laws of motion according to classical dynamics to examine a property of a multiparticle system composed of many particles. This method itself is relatively old but many improvements of this method have been proposed since 1980. Thus, the range of subjects capable of being studied by using the molecular dynamics method has been greatly expanded. This is because a method for performing a simulation under the conditions of constant temperature and pressure has been developed, although the phenomena were conventionally examined under the conditions of constant energy and volume.

In the field of computational physics, which concerns the development of new substances or materials, a method for non-empirically calculating molecular orbits is now practically used for development of small-molecule materials with small numbers of electrons. The cooperation of calculation, synthesis and substance property measurement is becoming a new style of a molecular development. On the other hand, for material design with multi-particles bodies of atoms and molecules comprising several hundreds to several thousands of atoms or several ten thousands of atoms depending on the subject, application of electronic theory is still difficult at present even though the capacity of computers approaches the order of GFLOPS. Classical molecular dynamics using a potential function between atoms or between molecules is, therefore, still used as the dominant method.

Before a computer simulation is introduced, statistical dynamics is used for examining the structure and properties of a group of many atoms and molecules based on microscopic information such as an interaction force applied between atoms. However, when the interaction force between atoms becomes rather complicated, it becomes impossible to obtain an exact solution of the basic formulas of statistical dynamics. The molecular dynamics method is a simulation method for applying Newton's equations for a multiparticle system in a numerical analysis and providing information similar to that obtained from the statistical dynamics method.

FIG. 1 (PRIOR ART) shows input information and output information according to the molecular dynamics method. As the input information, a potential function representing an interaction force applying between atoms or molecules and physical environmental conditions such as temperature and pressure are supplied. Newton's equations for multiparticle systems are solved under the potential function. Also, physical environmental conditions and the positional coordinates of an atom at successive points in time, which are obtained as the solution of the Newton equations, are subjected to statistical processing. Thermodynamics properties such as internal energy, and the elastic constant are provided as the output information. Further, the positional coordinates and velocities of the atoms at successive points in time are subjected to statistical processing, thereby providing dynamic properties such as the diffusion coefficient, viscosity coefficient, electrical conductivity and thermal conductivity, and spectroscopic properties as the output information.

The molecular dynamics simulation method uses as its subject a substance comprising a large number of molecules such as liquid and produces a motion of representative molecules by using a computer simulation, thereby providing macroscopic properties of the substance. By using a method of performing a simulation under conditions of constant temperature and pressure, it becomes possible to directly examine the arrangement of particles within a crystal and a structural phase transfer in which the form of the crystal changes. Naturally, the number of particles and the time used for the analysis is greatly limited by the computation calculation capability of the computer. The problem of the simulation is how to study a macroscopic property by using a small particle system in an efficient manner.

Next, the prior art relating to the constraint condition which is the subject of the present invention will be explained. FIG. 2 (PRIOR ART) shows an explanatory view of a bond, angle and torsion to explain the technical background of the present invention. FIGS. 3 and 4 are for explaining views of the constraint condition, FIGS. 5 and 6 show explanatory views of a predetermined constraint condition and FIGS. 7 and 8 are for explaining the potential function. When a constraint condition comprising a list of a constrained atom and a bond, angle and torsion of the constrained atom is generated to perform a simulation of the behavior of a molecule based on the molecular dynamics method by using a computer, conventionally, a user manually inputs the number of the atom and numerical values of bonds, angles and torsions in an input frame displayed on a display screen.

A bond constraining an atom is a bonding distance of two atoms I and J as shown in FIG. 2A. An angle is a bonding angle <IJK of three atoms I, J, K as shown in FIG. 2B. A torsion is an angle $\phi$ between a plane formed by three atoms, I, J, K and a plane formed by three atoms, I, L and K with two atoms I and K common to both planes with regard to four atoms I, J, K and L as shown in FIG. 2C.

Where the degrees of the freedom of the acetic acid molecule ($CH_3COOH$) with a chemical structure formula as shown in FIG. 3A are constrained to some extent, it is necessary to form a bond constraint list as shown in FIG. 3B, an angle constraint list as shown in FIG. 4A and a torsion constraint list as shown in FIG. 4B. The numbers 1 through 8 are attached to respective atoms in FIG. 3A for sequential numbering of the atoms within the molecule.

The contents of the bond constraint list shown in FIG. 3B represent that a distance between two atoms is constrained to a value provided as a bonding distance and  1 4 1.4 , for example, represent that the interatom bonding distance between H with the number 1 and C with the number 4 is constrained to be 1.4A. The contents of the angle constraint list shown in FIG. 4A represent that the angle is constrained to a value and  1 4 2 109.4 , for example, represents that the central angle 1-4-2 formed by H with the number 1, H with the number 2 and C with the number 4 is constrained to be 109.4° degrees.

Further the contents of the torsion constraint list shown in FIG. 4B represent that the torsion is constrained to the given value, and  4 5 7 8 180 , for example, represents that an angle $\phi$ between a plane 4-5-7 (namely, the plane formed by atoms 5, 4 and 7) and a plane 5-7-8 (namely, the plane formed by atoms 5, 8, and 7) is constrained to be 180° degrees.

A partial constraint may be applied, for example, only a torsion (4-5-7-8) of acetic acid shown in FIG. 5A is constrained, such that the torsion between plane 4-5-7 and plane 5-7-8 is constrained to be 180° degrees, for example. Then a bond constraint list, angle constraint list, and torsion constraint list as shown in FIGS. 5B to 5D are required. This is because when the torsion is constrained, the angle and bond forming the torsion should also be constrained.

Likewise, when only the angle (5-7-8) of acetic acid on FIG. 6A is constrained to be 109.4° degrees for example, the bond constraint list shown in FIG. 6B and the angle constraint list shown in FIG. 6C are required. This is because where the angle is constrained, all the bonds forming the angle should be constrained. The bond constraint list for constraining only the bond (5-7) is shown in FIG. 6D. As described above it should be noted in a given partial constraint that where the torsion is constrained, all the angles and the bonds forming the torsion should be constrained and where the angle is constrained, all the bonds forming the angle should be constrained. If these two conditions are not satisfied, a contradiction arises.

A bond potential function, angle potential function, or torsion potential function should be provided for a bond, angle or torsion to which a constraint is not applied the behavior of the molecule being simulated by using these potential functions. For example, a harmonic-type bond potential function is as shown in FIG. 7A and a harmonic-type angle potential function is as shown in FIG. 7C. A harmonic-type torsion potential function is as shown in FIG. 8A. When the bond potential function E(l) is partially differentiated with respect to variable (l), the force acting between atoms I and J in FIG. 2A is obtained. When the angle potential function E($\theta$) is partially differentiated with respect to variable $\theta$, the force acting between atoms I and K in FIG. 2B is obtained. When the torsion potential function E ($\phi$) is partially differentiated with respect to variable $\phi$, the force acting between atoms J and L in FIG. 2C is obtained.

When none of the bonds of the acetic acid molecule are constrained, the bond potential parameters as shown in FIG. 7B are required. Likewise, when none of the angles of the acetic acid molecule are constrained, the angle potential parameters as shown in 7D are required. When none of the torsions of the acetic acid molecule are constrained, under the condition that the bonds and angles are not constrained, the torsion potential parameters as shown in FIG. 8B are required.

When a simulation is performed based on the molecular dynamics method under a constraint condition in which some of the degrees of internal freedom within the molecule are frozen, conventionally a user has to prepare a constraint list as shown in FIGS. 3 and 4 manually and in advance, and input it into a simulator for use in the molecular dynamics method. Accordingly, the work efficiency is extremely low and thus the conventional manual method is not suitable for macromolecules having many atoms in a molecule.

When the torsion is constrained, all the angles and the bonds forming the torsion should be constrained. When the angle is constrained, all the bonds forming the angle should be constrained. However, these requirements are not always followed due to input of insufficient constraint conditions, thereby causing a contradiction and making the computation difficult.

Further, a potential function should be assigned to a torsion to which a constraint is not applied, as shown in FIGS. 7 and 8. But this is extremely troublesome and time consuming for an operator to perform such assignment manually.

SUMMARY OF THE INVENTION

An object of the present invention is to automatically generate constraint conditions necessary for an efficient simulation and to prevent a contradiction from arising in the constraint conditions, as the molecule structure information necessary for performing a molecular dynamics simulation is utilized.

A feature of the present invention resides in an apparatus for generating constraint conditions according to a molecular dynamics method for use in an apparatus which simulates the behavior of a molecule using a computer based on the molecular dynamics method, the constraint condition being for freezing some of the degree of the freedom within the molecule, constraint generation of the apparatus comprising a molecular structure information input processing unit for input of molecular structure information including "information on the atoms" forming the molecule and the bonding information of the atoms, bonding distance computing processing unit for computing processing the bonding distance of two bonded atoms (I, J) based on the input molecular structure information, and a bond constraint condition setting processing unit for maintaining a bond constraint list comprising the numbers of atoms in pairs whose bonds are constrained and the bonding distance information as the constraint condition.

BRIEF DESCRIPTION OF THE DRAWINGS

FIGS. 4A-4B show an explanatory view of a constraint condition relevant to the present invention;

FIGS. 7A-7D show an explanatory view of a potential function relevant to the present invention;

FIGS. 8A-8B show an explanatory view of a potential function relevant to the present invention;

FIG. 16 shows an example of a constraint condition generated in an embodiment according to the present invention;

FIG. 19 shows a second example of a display for use in explaining an embodiment of the present invention.

DETAILED DESCRIPTION OF THE PREFERRED EMBODIMENTS

Figure 1:
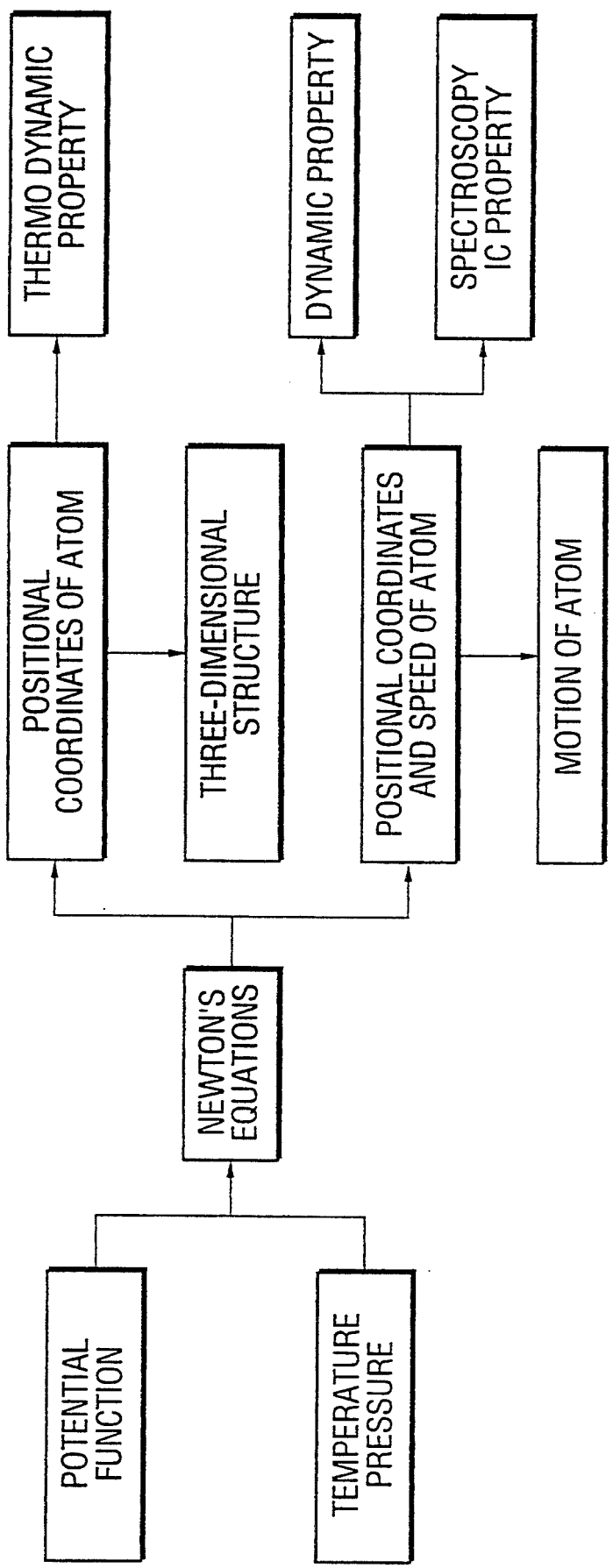
FIG. 1 (PRIOR ART) shows input and output information for use in a molecular dynamics method.
Figure 2A:
FIGS. 2A-2C (PRIOR ART) show an explanatory view of a bond, angle and torsion to explain the background of the present invention.
Figure 2B:
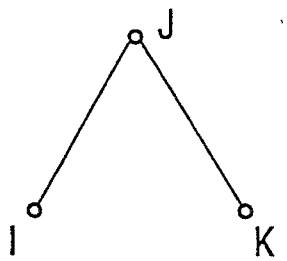
Figure 2C:
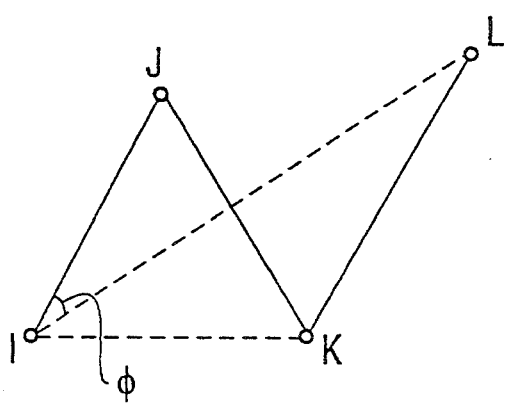
Figures 3A, 3B:
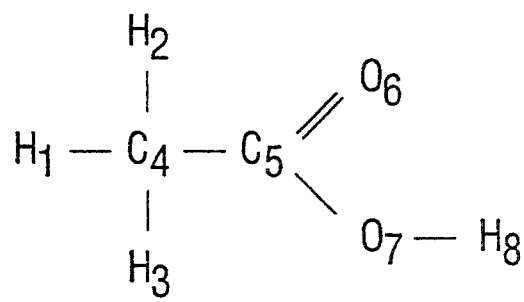
FIGS. 3A-3B show an explanatory view of a constraint condition relevant to the present invention.
Figures 5A, 5B, 5C, 5D:
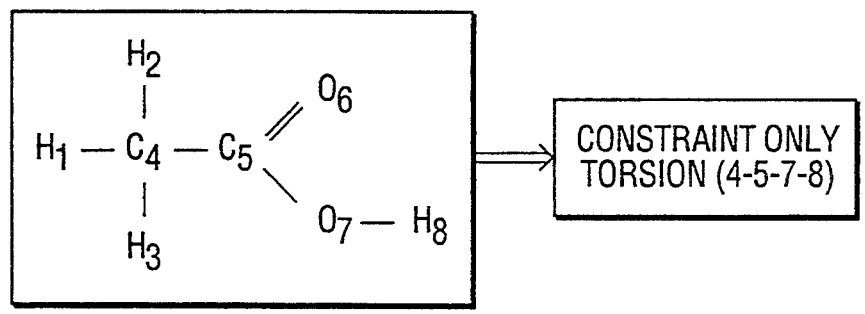
FIGS. 5A-5D present an explanatory view of a predetermined constraint condition relevant to the present invention.
Figures 6A, 6B, 6C, 6D:
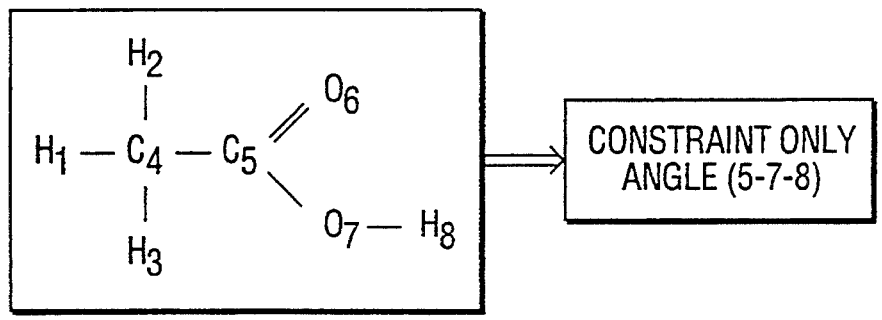
FIGS. 6A-6D show an explanatory view of a predetermined constraint condition relevant to the present invention.
Figure 9:
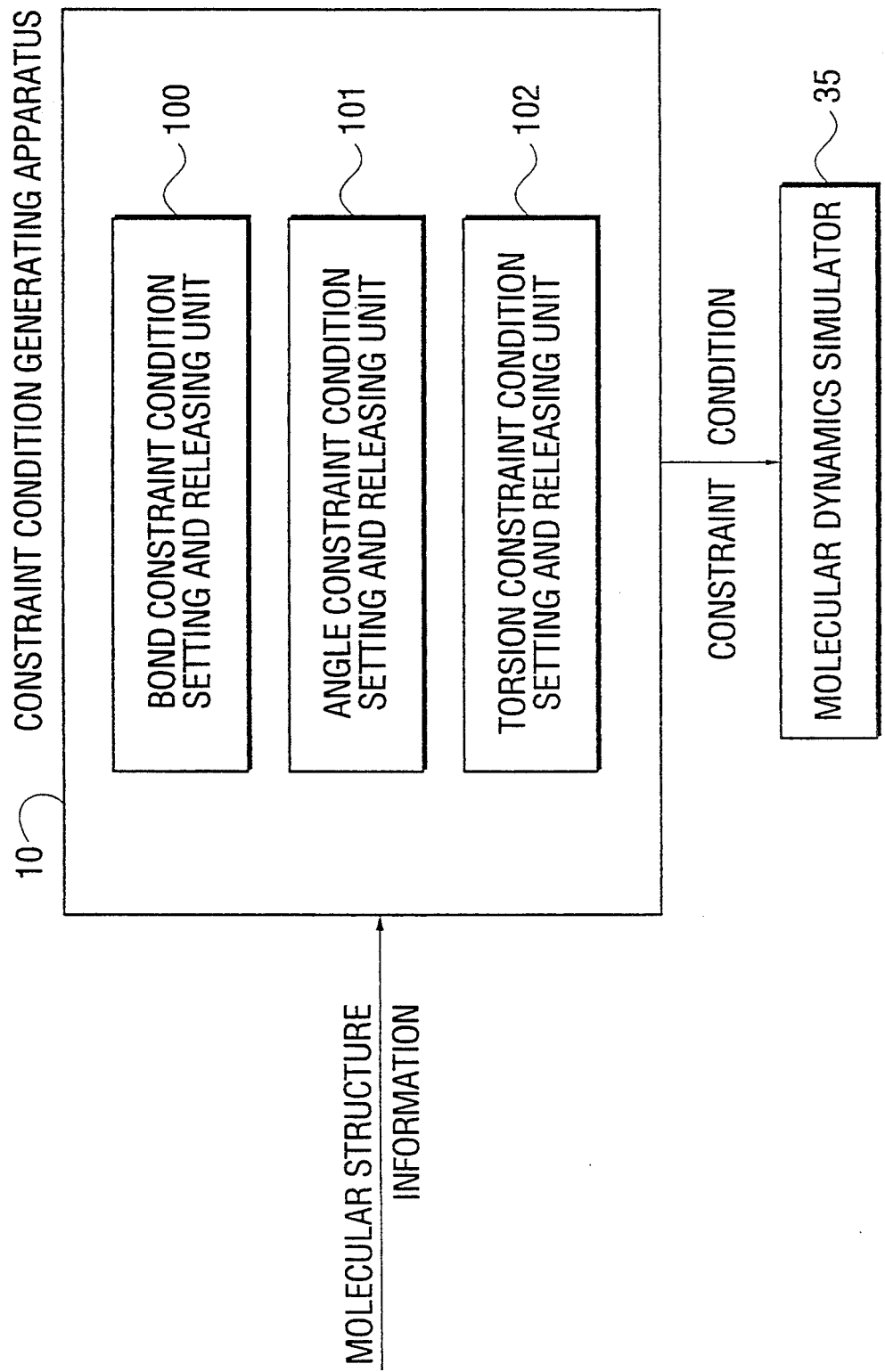
FIG. 9 shows a block diagram of a principle of the present invention.

FIG. 9 shows a block diagram of a principle structure of the present invention. Apparatus 10 for generating a constraint condition for a molecular dynamics method outputs a constraint condition required for molecular dynamics simulator 35 according to the molecular structure information and comprises unit 100 for setting and releasing a bond constraint condition, unit 101 for setting and releasing an angle constraint condition, and unit 102 for setting and releasing a torsion constraint condition.

In FIG. 9, the molecular structure information input to constraint condition generating apparatus 10 comprises atomic information of respective atoms forming a molecule such as a serial number, element symbol, x, y and z coordinates representing a position in three dimensional space and a bonding list designating how respective atoms are connected. Means 100 for setting and releasing the bond constraint condition calculates a bonding distance between two bonded atoms based on the input molecular structure information and sets a bond constraint list formed according to the serial numbers of the pairs and the bonding distances between atom pairs as a constraint condition, thereby performing a setting process. The setting and releasing unit 100 also performs a process of releasing the bond constraint condition by canceling the numbers of atoms in pairs by a user, and assigns a bond potential function to act between the atoms in the pairs for which the constraint is released: The user designates the pairs to be released using a mouse to select constraints from the bond constraint list and assigns a bond potential function to act between the two atoms for which the constraint is released, thereby setting parameters for the bond potential function.

When two pairs of atoms have an atom in common in the above described bond constraint list, the angle constraint condition setting and releasing unit 101 performs an angle constraint condition setting process by calculating the bonding distance of the two atoms which are not common to the two pairs of atoms and setting the angle constraint list so as to comprise the data of the calculated bonding distance and the serial numbers of the three atoms. Similar to the bond constraint condition releasing process, the angle constraint condition setting and releasing unit 101 cancels the numbers of the three atoms corresponding to the angle constraint condition which is required to be released in accordance with a designation by the user and assigns an angle potential function to the three atoms from which the constraint is released, as before setting a parameter for the angle potential function.

When two groups of three atoms forming angles in the angle constraint list have two atoms in common, the torsion constraint condition setting and releasing unit 102 calculates the bonding distance of the two atoms which are not common to the two groups and sets a torsion constraint list comprising the atom serial numbers and the data of the calculated bonding distances as a constraint condition of the angle formed between the two planes which are formed by the three-atom groups. Similarly, the torsion constraint condition setting and releasing unit 102 deletes the four atom serial numbers, forming the torsion from which the constraint is required be released in accordance with the designation by the user, from the torsion constraint list and assigns a torsion as before setting parameters for the torsion potential function.

Generally speaking, the molecular structure information is required when the behavior of the molecule is simulated by using the molecular dynamics method and thus the molecular structure information is always prepared. The present invention automatically generates a constraint condition for constraining all the degrees of freedom of the molecule, that is, constraining all the bonds, angles and torsions, by using the molecular structure information. When a constraint is not applied to all the atoms, a constraint list for constraining all the degrees of freedom is formed at first and the group of atoms for a point at which the constraint is to be released is designated by the user is deleted from the constraint list.

Therefore, the present invention can form the constraint condition effectively and quickly without involving any contradiction. The present invention automatically sets the data to be used for assigning the potential function with regard to a point to which the constraint is not applied.

The bond constraint condition setting and releasing unit 100 automatically generates the bond constraint list for constraining the degree of freedom of all the bonds through the constraint condition setting process and can partially apply the constraint of the bond through the bond constraint condition releasing process.

The angle constraint condition setting and releasing unit 101 automatically generates the angle constraint list for constraining the degrees of freedom of all the angles and the angle constraint releasing unit 101 applies partial constraints on the angles through the angle constraint releasing process.

Further the torsion constraint condition setting and releasing unit 102 automatically generates a torsion constraint list for constraining the all the torsions through the condition setting process and applies the constraint to some of the torsions through the torsion constraint condition releasing process.

Further the present invention displays the structure of the molecule which is the subject of the simulation, enabling a user to designate a combination of atoms, for corresponding to the bond, angle or the torsion in which the constraint should be released, in the displayed structure of the molecule. The constraint condition is thus released in accordance with the designation with a mouse by the user. For example, in the releasing process, if the bond which is to be released occurs in a group of three atoms forming a constrained angle or in four atoms forming a constrained torsion, a contradiction is caused by releasing the bond constraint condition and therefore the release of the bond constraint condition is automatically prohibited. Likewise a contradiction in which an angle is not constrained although the torsion in which the angle occurs is constrained is also prevented from occurring.

FIG. 10 shows a block diagram of a basic structure of the constraint condition generating apparatus according to the present invention. In FIG. 10A, the constraint condition generating apparatus 10 provided with a CPU and memory, is connected to a display 11 and mouse 12 for inputting a position on the display screen, and also connected to a molecular structure information storing device 13 for storing a position of an atom and bonding information of atoms in a molecule which is the subject of the simulation. The constraint condition generating apparatus 10 comprises a molecular structure information input processing unit 14 for inputting molecular structure information, a bonding distance computing processing unit 15 for computing a bonding distance routing to the bond, a bond constraint condition setting processing unit 16 for automatically calculating the constraint condition of the bond, a bonding distance calculating processing unit 17 for computing a bonding distance routing to an angle, an angle constraint condition setting processing unit 18 for automatically generating a constraint condition of an angle, a bonding distance computing processing unit 19 for computing a bonding distance routing to a torsion and a torsion constraint condition setting processing unit 20 for automatically generating a constraint condition of a torsion. The constraint condition generating apparatus also comprises a molecular structure display processing unit 21 for displaying a molecular structure on the display 11, and a constraint release subject selection unit 22 for inputting a pail of atoms for which the constraint is to be released, by using a mouse 12. The constraint condition generating apparatus 10 includes a bond constraint release prohibition processing unit 23 for prohibiting the constraint of the bond from being released when the release of the constraint of the bond is found not to be permissible after examination, bond constraint release processing unit 24 for releasing the constraint of a bond, and a bond potential function setting processing unit 25 for assigning a potential function to act between the atoms having the bond whose constraint is released. The constraint condition generating apparatus 10 further comprises an angle constraint release prohibition processing unit 26 for prohibiting the constraint of the angle from being released where the release of the constraint of the angle is found no to be permissible after examination, angle constraint release processing unit 27 for releasing the constraint of an angle, and potential function setting processing unit 28 for assigning a potential function to act between the atoms within the angle whose constraint is released. The constraint condition generating apparatus 10 includes a torsion constraint release processing unit 29 for releasing the constraint of a torsion, and a torsion potential function setting processing unit 30 for assigning a potential function to act between atoms with the torsion whose constraint is released.

The constraint condition generating apparatus 10 further includes a constraint condition storing apparatus 31 for storing the constraint conditions to be provided to the molecular dynamics simulator. The constraint condition storing apparatus 31 provides a bond constraint condition storing area 32 for storing the bond constraint conditions, an angle constraint condition storing area 33 for storing an angle constraint conditions and a torsion constraint condition storing area 34 for storing the torsion constraint conditions. Molecular dynamics simulator 35 performs a simulation of the behavior of a molecule based on the molecular dynamics method. Further a force field library storing apparatus 36 stores parameters relevant to potential functions, a bond constraint condition input processing unit 37 inputs the bond constraint condition to the bonding distance computing processing unit 17, and an angle constraint condition inputting processing unit 38 inputs the angle constraint condition to the bonding distance computing processing unit 19.

Figure 10A:
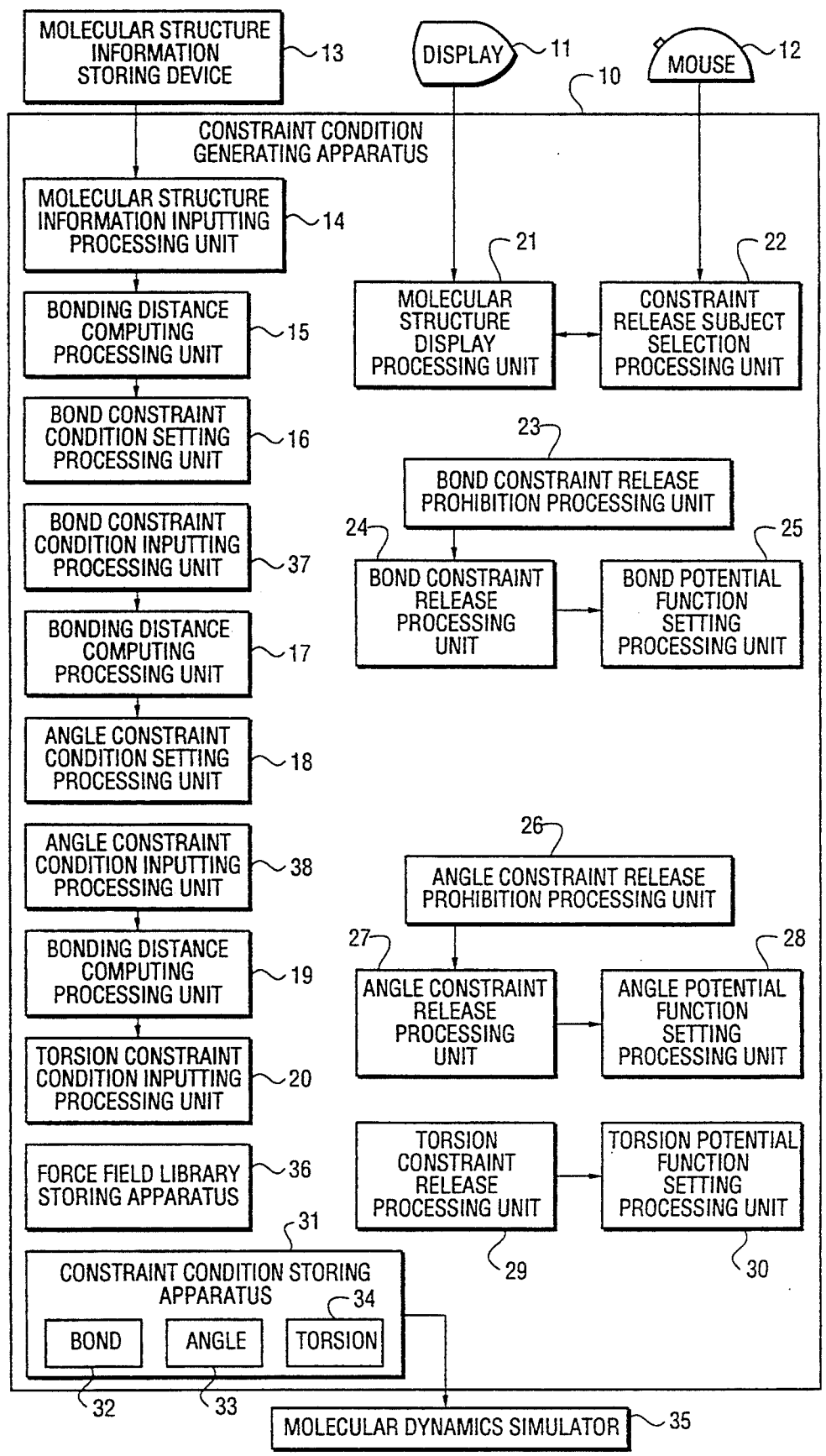
FIGS. 10A-10D show a block diagram of a basic configuration of a constraint condition generating apparatus according to the present invention.
Figure 10B:
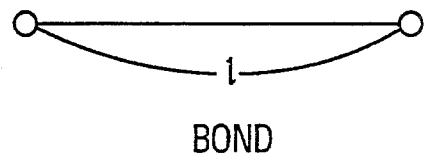

The molecule structure information input processing unit 14 inputs molecule structure information on atoms forming the molecule and the bonding information of the atoms from the molecule structure information storing apparatus 13. The bonding distance computing processing unit 15 calculates the bonding distance of two atoms (I, J) which are bonded as shown in FIG. 10B, based on the input molecule structure information.

The bond constraint condition setting processing unit 16 forms the bond constraint list comprising the serial numbers of atom pairs in which the bond obtained from the molecular structure information for constrained and the bonding distance information calculated based on the bonding distance computing processing unit 15 and thereby stores it in the constraint condition storing apparatus 31 as the constraint condition.

When releasing the bond constraint condition, the bond constraint release processing unit 24 cancels the numbers of atom pairs selected from the bond constraint list stored in the bond constraint condition storing area 32, and releases the constraints of the bonds formed by those atoms. The bond potential function setting processing unit 25 assigns the bond potential function, between two atoms in which the constraint is released, such as the force field library storing apparatus 36 of storing a table of potential parameters formed previously in accordance with the force field. The unit 25 uses the identifying name of the atom as a key, obtains parameters of a bond potential function and set it automatically.

Figure 10C:
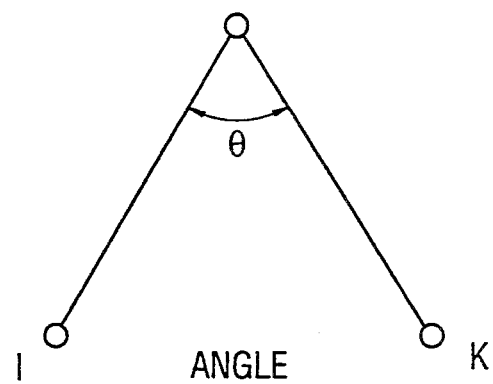

When setting the angle constraint condition is set, the bonding distance computing processing unit 17 extracts a pair of atoms (I, J) and (J, K) which are bonded with the common atom J as shown in FIG. 10C, from the bond constraint list stored in the bond constraint condition storing area 32, and computes the bonding distance of the two atoms (I, K) at the ends of the angle.

The angle constraint condition setting processing unit 18 forms an angle constraint list comprising the numbers of three-atom groups (I, J, K), and the bonding distance information of atom pairs (I, K), and stores it in the constraint condition storing apparatus 31 as the constraint condition of the central angle formed by the three atoms. The relation between the central angle and the bonding distance information of the atoms (I, K) will be described later.

When releasing the angle constraint condition, the angle constraint condition releasing unit 27 cancels the serials numbers of three-atom groups selected from the angle constraint list stored in the angle constraint list storing area 33, and releases the constraints of the angles formed by those three-atom groups. Then, angle potential function setting processing unit 28 assigns the angle potential function to act between two atoms in which the constraint is released, and searches the force field library storing apparatus 36 in which a table listing potential parameters is previously prepared in accordance with the force field, using the identifying name of the atom as a key, and obtains the parameters of the angle potential function and sets it automatically.

When setting the torsion constraint condition, the bonding distance computing processing unit 19 extracts two groups of three atoms (I, J, K) and (I, L, K) forming the angle as shown in FIG. 10B with two common atoms (I, K), from the angle constraint list stored in the angle constraint condition storing area 33, and computes the bonding distance of the two atoms (J, L) which are not common to above mentioned two groups. The torsion constraint list comprising the serial numbers of four atoms (I, J, K, L) and the bonding distance information of two atoms (J, L) computed by the bonding distance computing processing 19, is stored in the constraint conditions storing apparatus 31 as the constraint condition of angles formed between two planes, the planes each being are formed by three atoms. The relation between the angle formed by formed between planes and the bonding distance information of the two atoms (J, L) will be also explained later.

When releasing the torsion constraint condition, the torsion constraint releasing processing unit 29 cancels the numbers of atoms in a four-atom group from the torsion constraint list stored in the torsion constraint condition storing area 34, and then releases the constraint of the torsion of the four atoms. The torsion potential function setting processing unit 30 assigns the torsion potential function to act between four atoms in which the constraint is released, search force field library storing apparatus 36 in which a list of table of potential parameters previously prepared in accordance with the force field, by using the identification name of the atom as a key, obtains the parameter of the torsion potential function and automatically set the parameter.

According to the present invention, when the user selects a combination of atoms whose constraint is to be released, the molecular structure display processing unit 21 displays the molecular structure which is the subject on the display 11.

The constraint release subject selection processing unit 22 selects the combination of the atoms whose constraint is to be released, in accordance with the designation of the atoms in the molecular structure displayed on the display screen based on the designation of the user with mouse 12.

When the constraint of two atoms whose bond is constrained is released in accordance with the designation of the user, the bond constraint release prohibition processing unit 23 examines whether the two atoms to be released occur in a group of three atoms forming an angle which is constrained and prohibit the release of the constraint if they occur in a three-atom group. When two atoms, whose constraint is to be released, occur in a group of four atoms forming a constrained torsion, the bond constraint release prohibition processing unit 23 prohibits the release of the constraint.

When the constraint of three atoms whose angle is constrained is released in accordance with the designation of the user, the angle constraint release prohibition processing unit 26 examines whether the three atoms forming an angle whose constraint is to be released occur in a group of four atoms forming a constrained torsion, and prohibit the release of the constraint if they occur in a four-atom group.

Figure 11:
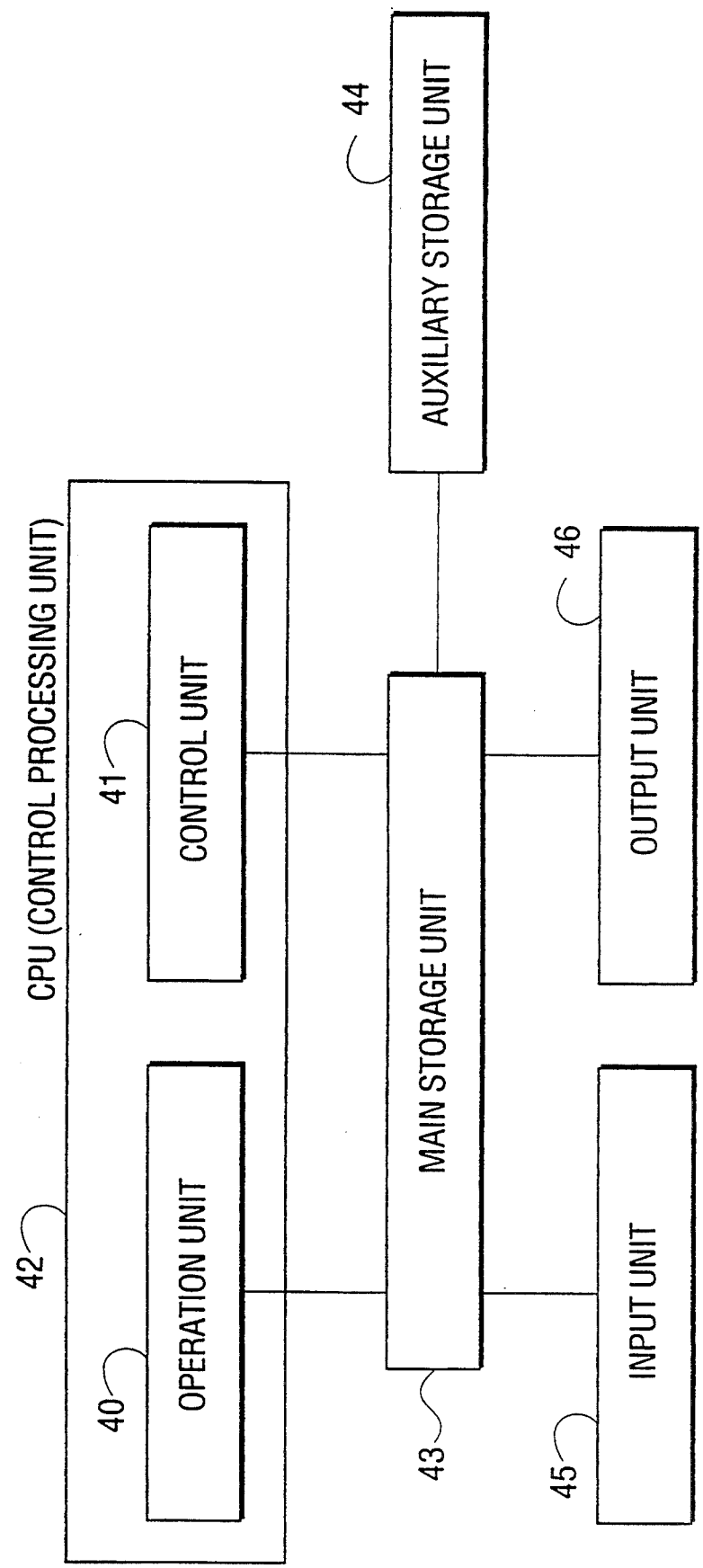
FIG. 11 shows a block diagram of a configuration of a computer system for use in realizing a constraint condition generating apparatus.

FIG. 11 shows a block diagram of the structure of a computing system for realizing the constraint condition generating apparatus according to the present invention. In FIG. 11, this system has a general structure comprising central processing unit (CPU) 42 provided with an operation unit 40 and a control unit 41, main storage unit 43, auxiliary storage unit 44 such as an external storage device input unit 45 and output unit 46.

The molecule structure information storing apparatus 13 and constraint condition storing apparatus 31 shown in FIG. 10 correspond to the auxiliary storage unit 44 shown in FIG. 11. CPU 42 performs various processes namely the input processes conducted by the molecule structure input processing unit 14, input processing units 37 and 38, setting processes conducted by the bond constraint condition setting processing unit, angle constraint condition setting processing unit 18 and torsion constraint condition setting processing unit 20, releasing processes conducted by the bond, angle and torsion releasing processing units 24, 27 and 29 and prohibiting processes conducted by the bond and angle constraint release prohibiting units 23 and 26.

The operation unit 40 shown in FIG. 11 performs various computing processes by means of bonding distance computing processing units 15, 17 and 19. Various potential function setting processing units 25, 28 and 30 set potential functions which are assigned at the same time as the release of the constraints. The contents of the force field library storing apparatus 36 for storing those potential functions and the parameters corresponding to them are also stored in the auxiliary storage unit 44. The molecular structure display processing unit 21 outputs the structure of the molecule which is the subject of the simulation on the display 11 in accordance with an instruction from CPU 42. The constraint release target selection unit 22 selects the constraint release target designated by user by using the mouse 12 corresponding to the input apparatus 45.

A concrete example of the molecule structure information and a flowchart of various processes will be explained in more detail.

Figures 12A, 12B, 12C:
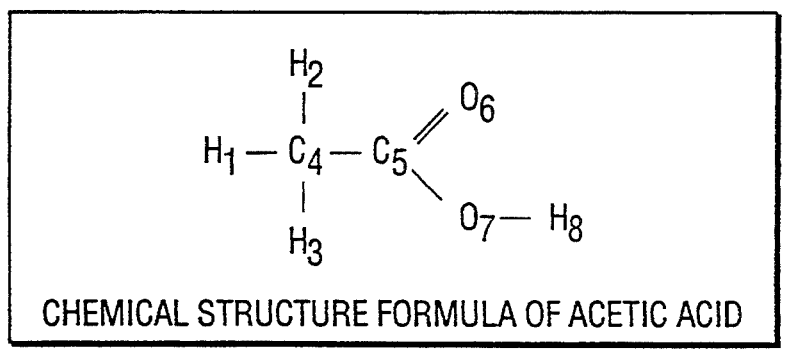
FIG. 12 shows an explanatory view of molecular structure information to be used in an embodiment of the present invention.
Figure 13:
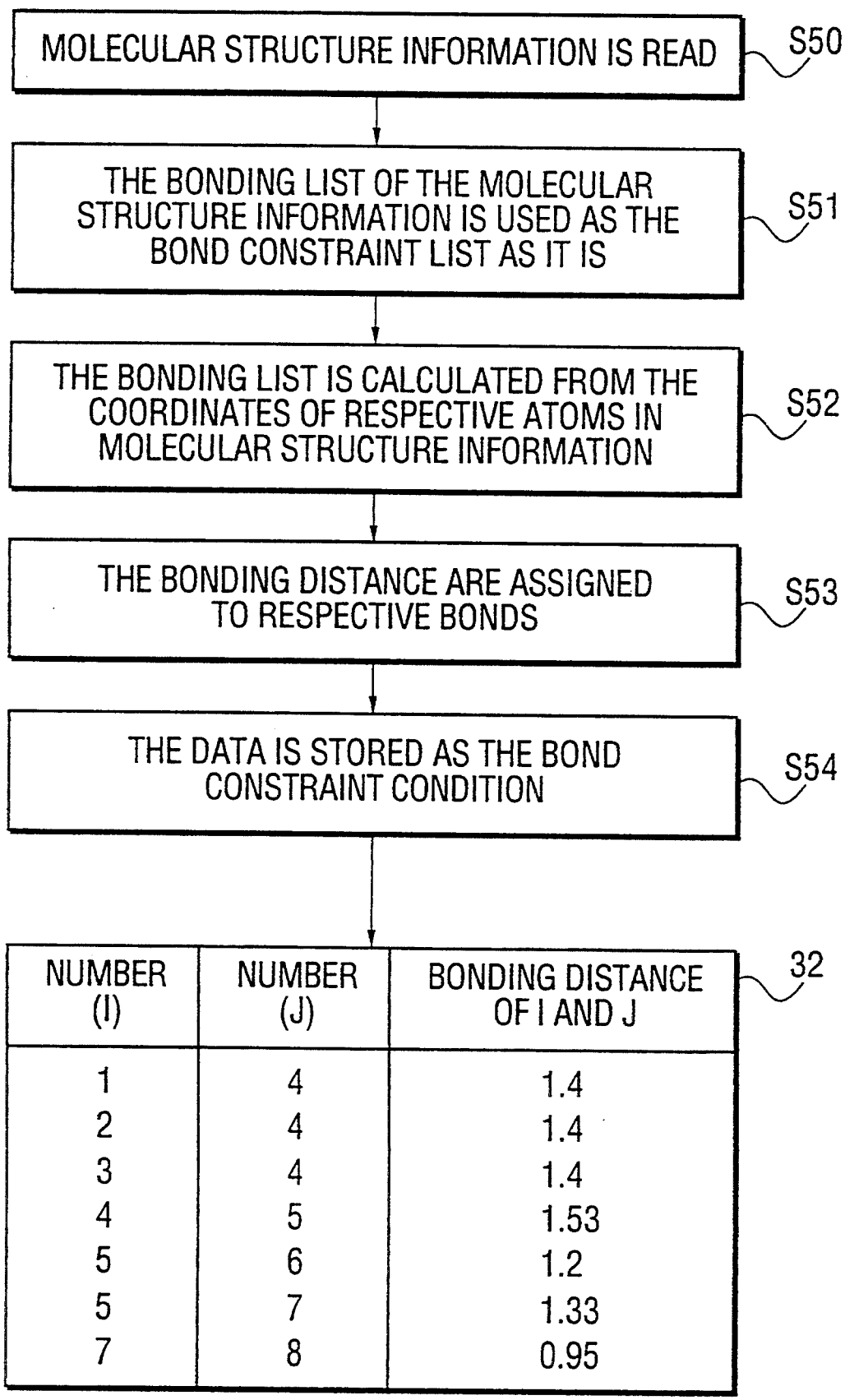
FIG. 13 shows a flow chart of the process of generating a bond constraint condition in an embodiment of the present invention.
Figure 14:
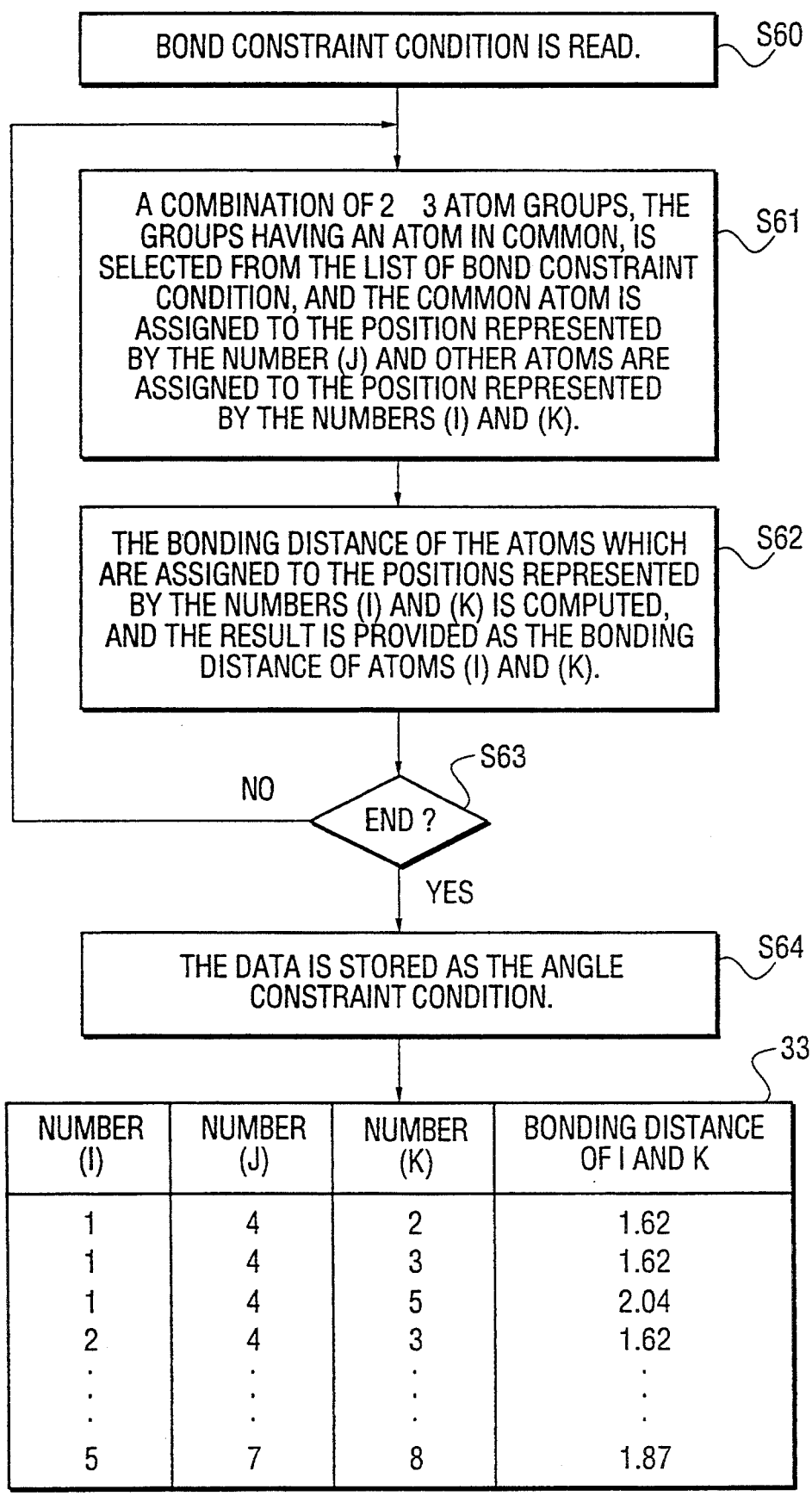
FIG. 14 shows a flow chart of the process of generating an angle constraint condition in an embodiment according to the present invention.
Figure 15:
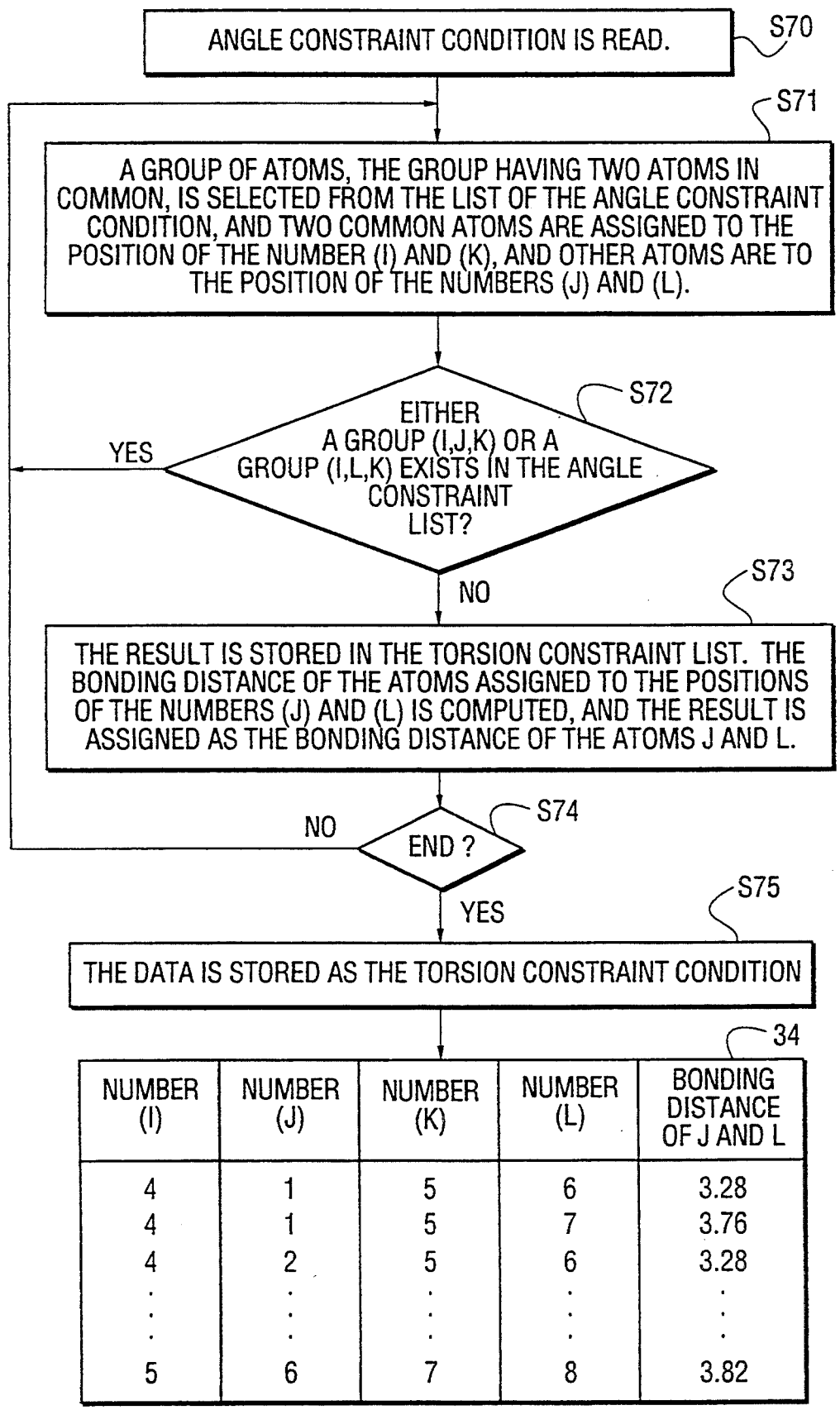
FIG. 15 shows a flow chart of the process of generating a torsion constraint condition in an embodiment according to the present invention.
Figure 17:
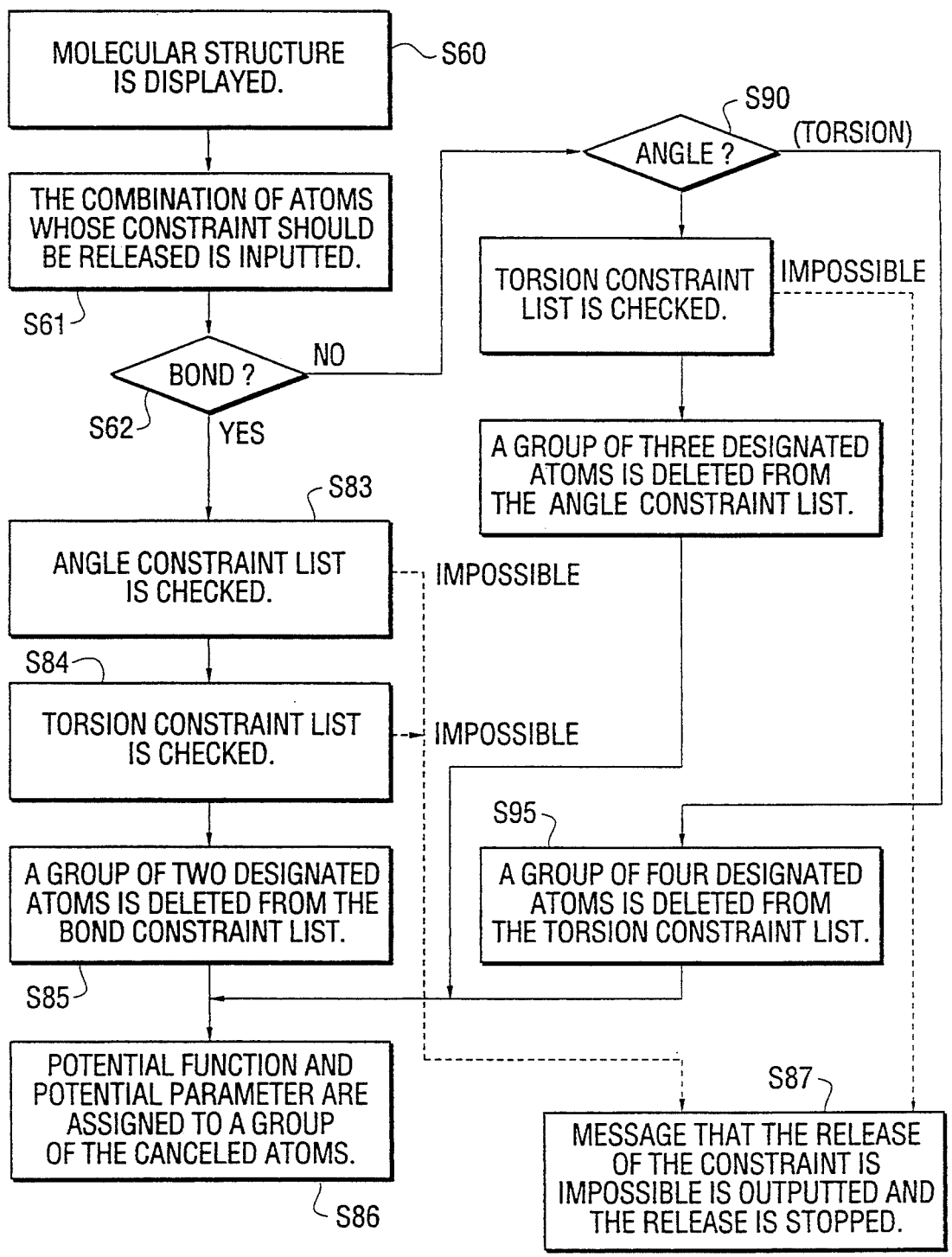
FIG. 17 depicts a flow chart for releasing a constraint condition in an embodiment of the present invention.

FIG. 12 shows an explanatory view of molecule structure information to be used in an embodiment of the present invention, FIG. 13 shows a flow chart of the bond constraint condition generating process in accordance with an embodiment of the present invention, FIG. 14 shows a flow chart of the angle constraint condition generating process in the embodiment of the present invention, FIG. 15 shows a flow chart of the torsion constraint condition generating process in the embodiment of the present invention, FIG. 16 shows an example of the constraint conditions generated in accordance with the embodiment of the present invention, and FIG. 17 shows a flow chart of the constraint release process in the embodiment of the present invention.

The embodiment of the present invention will be explained by referring to an example of acetic acid ($CH_3COOH$) with a chemical structure as shown in FIG. 12A. The numbers 1 to 8 attached to respective atoms in the molecule of acetic acid shown in FIG. 12A are the serial numbers of the atoms within the molecule. When the behavior of the molecule is simulated using the molecule dynamics method, the atomic information shown in FIG. 12B and the bonding list of the atoms shown in FIG. 12C are required, and are therefore previously prepared as input information to the molecule dynamics simulator. The present invention automatically generates the bonding constraint conditions, angle constraint conditions and the torsion constraint conditions by using the previously prepared a molecular structure information as explained hereinafter.

The atomic information part of the molecular structure information comprises the serial numbers of the atoms forming the molecule, the element symbol of the atom, and the positional information of the atoms in x, y, and z coordinates. The bonding list shows pairs of serial numbers representing bonded atom pairs.

The bond constraint conditions are generated in steps S50 to S54 in FIG. 13 in accordance with the molecular structure information, and therefore is explained in accordance with these steps S50 to S54.

First, the atomic information and bonding list shown in FIGS. 12B and 12C are read from the molecular structure information storing apparatus 13 shown in FIG. 10. This process is performed by the molecular structure information input processing unit 14 shown in FIG. 10.

Next, at step S51, the bonding list of the molecular structure information is used as the bond constraint list, as it is, this is conducted by the bond constraint condition setting processing unit 16.

At step 52, the atomic information part of the molecular structure information is referred to and the bonding distances are calculated from the coordinates of respective atoms. This step is performed by the bonding distance computing unit 15.

At step 53, the bonding distances computed at step S52 are assigned to respective bonds in the bond constraint list. This assignment is performed by the bond constraint condition setting processing unit 16.

As step S54, the bond constraint list to which the bonding distance is assigned and is stored in the bond constraint condition storing area 32 as the bond constraint condition. In other words, the bond constraint conditions are stored in the constraint condition storing apparatus 31.

The angle constraint conditions are generated in accordance with the steps S60 to S64 shown in FIG. 14 based on the bond constraint condition generated by the process shown in FIG. 13.

At step S60, the bond constraint conditions are read from the bond constraint condition storing area 32. The bond constraint condition is input by the bond constraint condition input processing unit 37.

At step S61, the angle constraint condition setting processing unit 18 selects from the list of bond constraint conditions a combination of atoms, having one atom in common and assigns the common atom to the position represented by the number (J) and the other atoms to the position represented by the numbers (I) and (K).

At step S62, the bonding distance computing unit 17 computes the bonding distance of the atoms which are assigned to the positions represented by the numbers (I) and (K). The result of the computation is provided as the bonding distance of atoms (I) and (K) by angle constraint condition setting processing unit 18. The above steps S61 and S62 are repeated with regard to all the combinations of pairs of atoms in the bond constraint list that have an atom in common.

When the assignment of angle constraint conditions is completed at step S63, the angle constraints comprising groups of serial numbers (I), (J) and (K) and bonding distances between (I) and (K) are stored in the angle constraint condition storing area 33 as the angle constraint conditions at step S64. That is, the angle constraint conditions are stored in the constraint condition storing apparatus 31.

The torsion constraint conditions are generated in steps S70 to 75 shown in FIG. 15 based on the angle constraint conditions prepared through the process shown in FIG. 14.

At step S70, the angle constraint conditions are read from the angle constraint condition storing area 33. The angle constraint condition is input by the angle constraint condition input processing unit 38.

Next, at step S71, the torsion constraint condition setting processing unit 20 selects from the list of angle constraint conditions a group of atoms, the groups having two atoms in common and the two common atoms are assigned to the positions represented by the number (I) and (K) and other atoms are assigned to the positions represented by the numbers (J) and (L).

Subsequently, at step S72 it is checked examined whether either a group (I, J, K) or a group (J, L, K) does not exist in the angle constraint list. If it does not exist, process proceeds to the step S73. If it does not exist, the process returns to the step S71 and searches for other pairs of groups.

Further, at step S73, the serial numbers of the atoms (I), (J), (K) and (L) are stored in the torsion constraint list, and the bonding distance computing processing unit 19 computes the bonding distance between the atoms assigned to the positions (J) and (L). The torsion constraint condition setting processing unit 20 assigns the result of the computation as the bonding distance of the atoms J and L. The above steps S71 to 73 are repeated for all groups of angles in the angle constraint list having atoms in common.

When the assignment is completed at step S74, the torsion constraint list to which the bonding distances of atoms J and L are assigned is stored in the torsion constraint condition storing area 34 as torsion constraint condition at the step S75. That is, the torsion constraint conditions are stored in the constraint conditions storing apparatus 31.

The bond constraint conditions, angle constraint conditions and the torsion constraint condition which are generated by the processes shown in FIGS. 13 through 15 are combined to provide the constraint conditions for constraining all the degrees of freedom of the acetic acid molecule. The constraint conditions thus obtained are as shown in FIG. 16A to C. The angles and torsions are specified as angle values in the form of the angle constraint list shown in FIG. 4A and torsion constraint list shown in FIG. 4B, but they are specified as bonding distance values in FIG. 16. The angles of FIGS. 4A and 4B corresponds to the bonding distances of FIG. 16.

That is the angle $\theta$ used as the angle constraint condition is provided by the following expression $$\theta + \cos^{-1}(r_{ij} \cdot r_{kj} / |r_{ij}| \cdot |r_{kj}|)$$

Where the vector from the atoms I to J is expressed by $\vec{r}_{ij}$ and the vector from the atoms K to J is expressed by $\vec{r}_{kj}$ as shown in FIG. 10C.

Figure 10D:
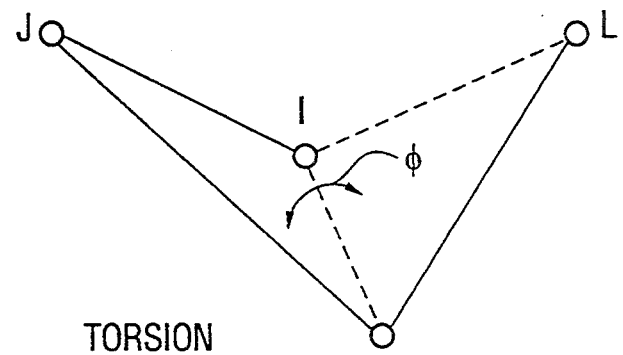

The angle $\phi$ used as the torsion constraint condition is shown by the following formula $$\phi = \cos^{-1}(p \cdot q / |p| \cdot |q|)$$

where $$p = r_{ji} \cdot r_{kb} \quad q = r_{ki} \cdot r_{li}$$

in accordance with the representation shown in FIG. 10D.

When the constraint is released, first it is specified which degree of freedom requires release, whether bond, an angle or a torsion, and the atoms forming the portion to be released are designated. Then, the designated atoms are canceled from the constraint list. When an angle constrain is release, the constraint is released only when the group of three atoms forming the angle does not exist in the torsion constraint list. When a constraint of a bond is released, the constraint can be released only when the group of two atoms forming the bond does not exist in the angle constraint list or the torsion constraint list. It should be noted that only the user can request the release of the constraint. A potential function and the potential parameters are assigned to the released portion in accordance with the bond, the angle and the torsion. The above process is shown in the flowchart of FIG. 17. Steps S80 to S95 shown in FIG. 17 will be explained.

At step S80, the molecular structure of the release is displayed on the display 11 when the release of the constraint of a bond, an angle or a torsion is to be specified.

At step S81, a group of the atoms hit by the mouse 12 on the display screen is treated as the subject of the release of the constraint. When the constraint of a bond is to be released as the result of the decision in step S82, the steps following the step S83 are executed. In other cases, the process proceeds to the step S90.

When the constraint of the bond is released, at step S83 the angle constraint list is examined. It is checked whether the designated atom pair exists in a group of atoms in the angle constraint list. If it exists, the release is deemed as impossible in the step S87.

Next, at step S84 the torsion constraint list is examined, and it is checked whether the designated atom pair exists in a group of atoms in the torsion constraint list. If it exists, the release is impossible and the process proceeds to step S87.

Where the designated group of two atoms does appear in neither the angle constraint list nor the torsion constraint list, the group of the atoms is deleted from the bond constraint list at step S85.

At step S86 the potential function and potential parameters are assigned to the canceled group of atoms in accordance with the bond, angle or torsion. The potential parameter can be obtained by searching the force field library storing the value predetermined by the method of obtaining the force field at the table list by using the identification name of the atom as a key.

At step S90, when the constraint of an angle is to be released, the process proceeds to the step S91. When the constraint of the torsion is to be released, the process proceeds to step S95. At step S91 the torsion constraint list is examined, and it is checked whether the designated group of three atoms exists in a group of atoms in the torsion constraint list. If it exists, the release is impossible and the process proceeds to the step S87.

When the designated group of three atoms does not appear in the torsion constraint list, the group of atoms are deleted from the angle constraint list at step S92 and the process to step S86 thereby performing an assignment of the potential function and the potential parameters.

When the constraint of an torsion is to be released the designated group of four atoms is deleted from torsion constraint list at step S90.

Where the release of the constraint is impossible according to the checking processes performed at the step S83, S84 or S91 the step S87 outputs the message that the release of the constraint is impossible and stops the release of the constraint of the group of atoms.

Figure 18A:
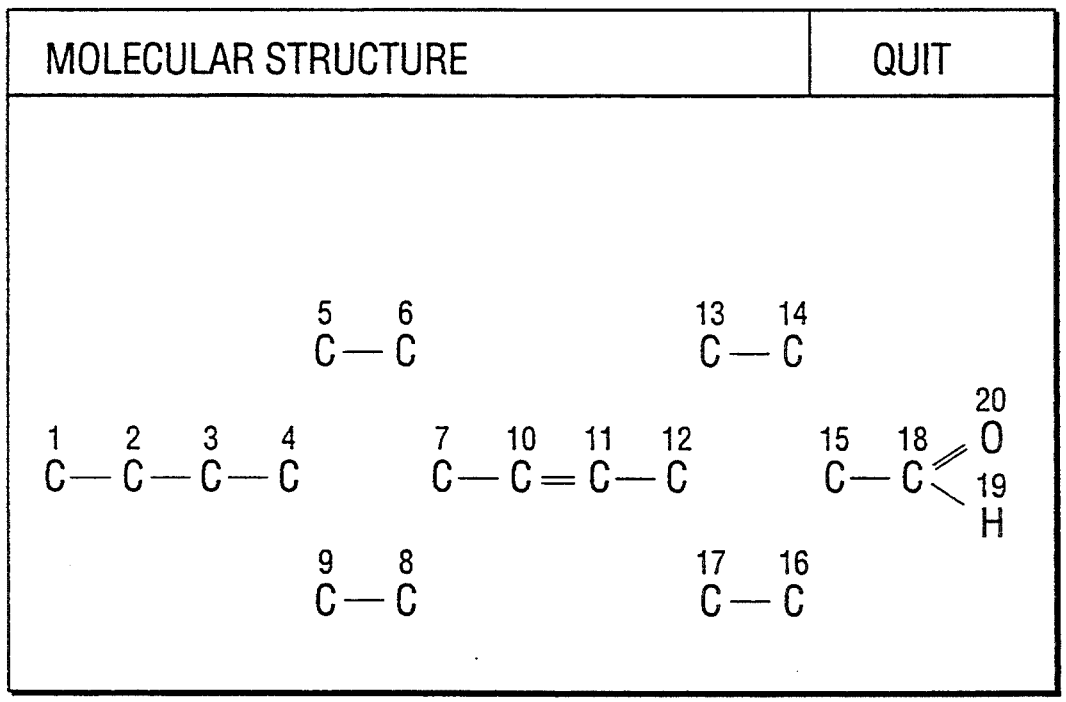
FIG. 18 shows a first example of a display for use in explaining an embodiment of the present invention.
Figure 18B:
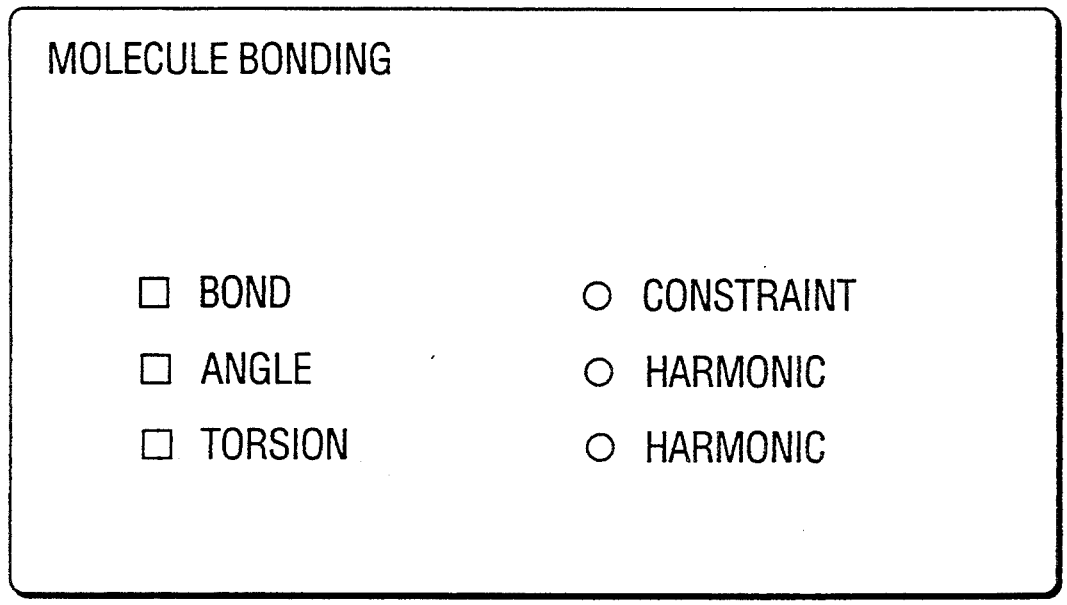

Next, an example of an operation and embodiment of the present invention will be explained with reference to the example of the display shown in FIGS. 18 to 20.

In response to the request for display of the molecular structure of the subject to be processed the molecular structure shown in FIG. 19A for example is displayed together with the serial numbers of the atoms in accordance with the molecular structure information. The specification of the constraint condition is performed in accordance with the screen shown in FIG. 18B for example. It should be noted that the bond between atoms 4–5, 6–7, 4–9, 7–8, 12–13, 12–17, 14–15 and 15–16 are not shown but FIG. 18A as a whole represents one molecule.

Any one of constraint, harmonic function type and unharmonic function type can be selected for respective constraint of the bond, angle and torsion by using a cyclic menu shown by a circle mark. However, when an angle is constrained, the bond must be constrained beforehand. When a torsion is constrained, both the relevant bonds and the relevant angles must be constrained beforehand. In accordance with such condition, the color of the mark, that is, the line representing the bond between two atoms in the molecular structure shown in FIG. 18A changes and is displayed in the sequence white, red, blue and light blue color.

Examples of unharmonic functions are as follows in correspondence with the harmonic functions explained by referring to FIG. 7 to 8.

$$E(l) = K_B(l-l_o)^2 [1 - K_1(l-l_1) + K_2(l-l_2)^2]$$

$$E(\theta) = K_A(\theta - \theta_o)^2 [1 - k_1'(\theta - \theta_1) + K_2'(\theta - \theta_2)^2]$$

$$E(\phi) = K_T(1 + \cos \phi) + K_T'(1 - \cos 2\phi) + K_T'(1 + \cos 3\phi)$$

Where $K_1$, $K_2$, $K_1'$, $K_2'$, $K_T'$, $K_{T2}'$, $L_1$, $L_2$, $\theta_1$ and $\theta_2$ in these expressions are parameters as similar to $K_B$ in FIGS. 7 and 8.

FIG. 19 shows an example of the display of the potential list (parameter) of the kind in which the constraints do not exist for the bond angles and torsions. A scroll of the display in an upwards or downwards direction is made possible by clicking upwards and downwards. The example of the display of this list is not related to the example of the molecule shown in FIG. 8A.

The force constant in the bond potential list in FIG. 19 corresponds to parameter $K_B$ explained by referring to FIG. 7B. The bond length designates parameter $l_o$, the force constant in the angle potential list represents parameters $K_A$, the bond angle shows parameter $\theta_o$, the force constant in the torsion potential list represents parameter $K_T$ shown in FIG. 8B, and CN corresponds to parameter $\phi_o$.

The parameter value other than the ID which designates a group of serial numbers of the atoms can be corrected by moving a cursor. After a correction is completed, "done" is clicked and then the corrected value is retained and stored. When "cancel" is clicked, the corrected value is not retained and the screen disappears.

Figure 20:
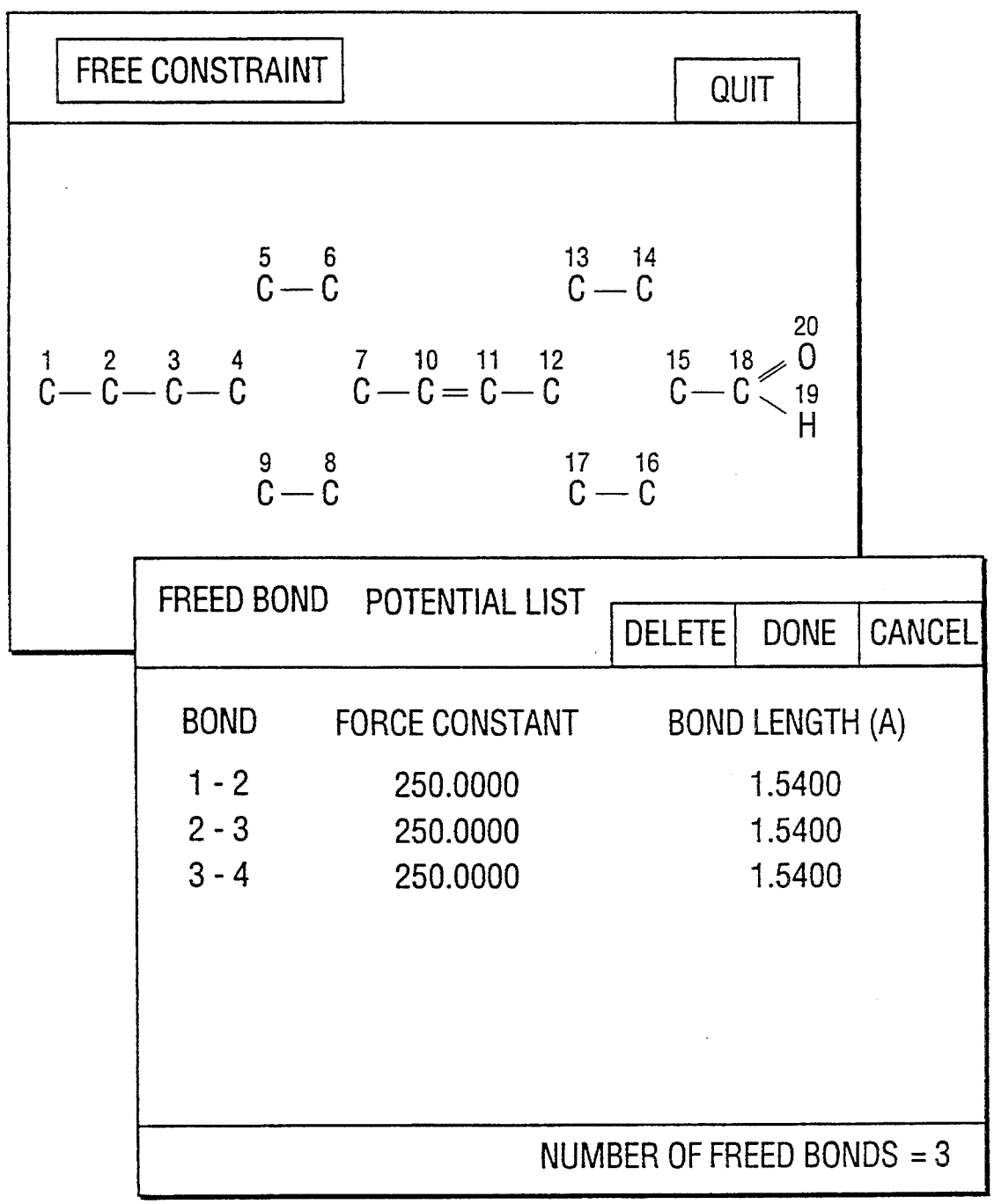
FIG. 20 shows the third example of a display for use in explaining an embodiment of the present invention.

When the bond constraints are specified, an option called "free constraint" is available on the screen on which the molecule structure is displayed, as shown in FIG. 20. If "free constraint" is not clicked, all the bonds are constrained in accordance with the automatic constraint condition generation of the present invention. After the bonds have been constrained and some of the constraint is released, and then "free constraint" should be to be clicked. A display frame of the bond potential list in which the constraints appear is then displayed. At this time, the bond whose constraint is to be released is specified by clicking two atoms using the mouse and then the constraint of the bond at that point is released and the released bond is displayed in the bond potential list.

For example, if the bond between the atoms 1 and 2, 2 and 3, and 3 and 4 are to be released in the molecular structure shown in FIG. 20, the atoms 1 and 2, 2 and 3, 3 and 4 are clicked. As a result, the color of the bonds changes accordingly and a list of the released bond is displayed in the bond potential list as shown in display frame at the lower part of FIG. 20.

A part of the bond list in the released bond potential list is clicked and "delete" in the menu is clicked the that torsion of the bond list is deleted and constained again. At this time, line correcting atoms is returned to the original color. When two or three torsion of the bond list are to be deleted simultaneously in the delete operation, the torsion to be deleted in the bond list is sequentially designated and thereafter "delete" is clicked, thereby it is possible to proceed the deletion of these torsions.

When "cancel" is clicked the display return to the state, namely, in which all the bonds are constrained. And thus the screen is screen ends. If there is no more bonds to be released, "done" clicked, thereby finally determining the bond to be released.

Where the constraint of the angle and torsions are to be released, the operation similar to the above operation can be conducted.

As explained above, according to the present invention, the constraint condition used for the simulation based on the molecular dynamics method can be generated effectively within a short time, and without any contradiction. As the data for assigning potential function is automatically generated with regard to the torsions to which the constraint is not applied the calculation and computation based on the molecular dynamics method can be conducted with ease.

The present invention can be applied to an industrial field in which it is required to develop of a substance or material and analysis of their property using a molecular dynamics method.

What is claimed is:

1. An apparatus for generating constraint conditions for use in an apparatus for simulating the behavior of a molecule by using a computer based on a molecular dynamics method, the constraint conditions freezing a part of the degree of the internal freedom within the molecule, comprising:

molecular structure information input processing means for inputting molecular structure information including atomic information on atoms forming a molecule and information on the bonding between the atoms;

bonding distance computing processing means for computing a bonding distance of two bonded atoms (I, J) based on the input molecular structure information;

bond constraint condition setting processing means for generating a bond constraint list including numbers of two atoms whose bonds are constrained, based on the computed bonding distance, as the constraint conditions; and means for using said generated constraint conditions in a molecular dynamics simulator to simulate a behavior of the molecule.

2. An apparatus for generating constraint conditions for use in an apparatus for simulating the behavior of a molecule by using a computer based on a molecular dynamics method, the constraint conditions freezing a part of the degree of the internal freedom within the molecule, comprising:

bond constraint condition storing means for storing a bond constraint list including numbers of two atoms whose bonds are constrained based on bonding distance information;

bond constraint releasing process means for releasing the constraint of the bond of two atoms by deleting the number of two atoms from the bond constraint list;

bond potential function assignment processing means for setting a bond potential function between the two atoms whose constraint are released by the bond constraint releasing process means and for setting a parameter bond potential function; and means for using the bond potential function and the parameter bond potential function in a molecular dynamics simulator to simulate a behavior of the molecule.

3. The constraint condition generating apparatus as claimed in claim 2 comprising the bond constraint release prohibition processing means for prohibiting the release of a constraint when the two atoms of a constraint to be released exist in a group of three atoms forming the constrained angle or exist in a group of four atoms forming a constrained torsion when the constraint of two atoms whose bond is constrained is released.

4. An apparatus for generating constraint conditions for use in an apparatus for simulating the behavior of a molecule by using a computer based on a molecular dynamics method, the constraint conditions freezing a part of the degree of the internal freedom within the molecule, comprising:
  bond constraint condition storing means for storing a bond constraint list including numbers of two atoms whose bonds are constrained based on bonding distance information;
  bonding distance computing processing means for computing the bonding distance of two atoms (I, K) at both ends where two bonded groups of atoms (I, J) and (J, K) have a common atom J in the bond constraint list;
  angle constraint condition setting processing means for generating an angle constraint list comprising the numbers of three atoms (I, J, K) bonding distance information of two atoms (I, K) at both end as the constraint condition of a central angel formed by three atoms; and
  means for using said generated constraint condition in a molecular dynamics simulator to simulate a behavior of the molecule.

5. An apparatus for generating constraint conditions for use in an apparatus for simulating the behavior of a molecule by using a computer based on a molecular dynamics method, the constraint conditions freezing a part of the degree of the internal freedom within the molecule, comprising:
  bond constraint condition storing means for storing a bond constraint list including numbers of two atoms whose bonds are constrained based on bonding distance information;
  angle constraint condition storing means for storing an angle constraint list including numbers of three atoms whose angles are constrained, bonding distance information of two atoms at both ends, as the constraint condition;
  angle constraint release processing means for releasing the constraint of an angle formed by three atoms by deleting the numbers of the three atoms from the angle constraint list;
  angle potential function setting processing means for assigning an angle potential function between three atoms whose constraint are released and for setting a parameter of the angle potential function; and
  means for using the angle potential function and the parameter in a molecular dynamics simulator to simulate a behavior of the molecule.

6. The constraint condition generating apparatus as claimed in claim 5 comprising angle constraint condition prohibit processing means when three atoms forming the angle to be released exist in a group of four atoms forming the constraint torsion when the constraint of three atoms whose angle is constrained is released.

7. An apparatus for generating constraint conditions for use in an apparatus for simulating the behavior of a molecule by using a computer based on a molecular dynamics method, the constraint conditions freezing a part of the degree of the internal freedom within the molecule, comprising:
  bond constraint condition storing means for storing a bond constraint list including numbers of two atoms whose bonds are constrained based on bonding distance information;
  angle constraint condition storing means for storing an angle constraint list including numbers of three atoms whose angles are constrained bonding distance information of two atoms at both ends as the constraint condition;
  bonding distance computing processing means for computing the bonding distance of two atoms (J, L) where the three atoms (I, J, K) and (I, L, K) have two common atoms (I, K) in the angle constraint list;
  torsion constraint condition setting processing means for generating a torsion constraint list comprising the numbers of four atoms (I, J, K, L) and the bonding distance information of two atoms (J, L) as the constraint condition of the angle formed between the two planes of two respective groups of three atoms; and
  means for using said generated constraint condition in a molecular dynamics simulator to simulate a behavior of the molecule.

8. An apparatus for generating constraint conditions for use in an apparatus for simulating the behavior of a molecule by using a computer based on a molecular dynamics method, the constraint conditions freezing a part of the degree of the internal freedom within the molecule, comprising:
  bond constraint condition storing means for storing a bond constraint list including numbers of two atoms whose bonds are constrained based on bonding distance information;
  angle constraint condition storing means for storing an angle constraint list including numbers of three atoms whose angles are constrained bonding distance information of two atoms at both ends as the constraint condition;
  torsion constraint condition storing means for storing the torsion constraint list comprising the numbers of four atoms whose torsions are constrained, and the bonding distance of two atoms which are not positioned on an access on the common access of the two planes of the torsion, as the constraint conditions;
  constraint release processing means for releasing the constraint of a torsion formed by four atoms by deleting the numbers of the four atoms from the torsion constraint list;
  torsion potential function setting processing means for assigning a torsion potential function between four atoms whose constraint is released and for setting a parameter of the torsion potential function; and
  means for using the torsion potential function and the parameter in a molecular dynamics simulator to simulate a behavior of the molecule.

9. The constraint condition generating apparatus as claimed in claim 8 comprising a molecular structure display processing means for displaying the molecular structure of the subject when a group of atoms whose constraints are to be released is selected and constraint release subject processing means for selecting group of atoms in a molecular structure on the display in respond to input from a screen position input apparatus.

10. A constraint condition generating apparatus for generating a constraint condition to be output to a molecular dynamics simulator simulating a behavior of a molecule according to a molecular dynamics method under the constraint condition for freezing at least a part of a degree of a freedom within the molecule, comprising:

bond constraint condition setting and releasing means (100) for setting a bond constraint list comprising the number of two atoms whose bond are to be constrained and a bonding distance between two atoms for an input of molecular structure information comprising an atom forming the molecule and bonding information of the atom, and for releasing the constraint of the bond of two atoms, by canceling the numbers of two atoms whose bond are constrained with regard to a part of bonds in said bond constraint list in accordance with a designation by a user;

angle constraint condition setting and releasing means for setting an angle constraint list comprising an angle constraint condition designating a combination of the number of three atoms comprising two atoms which are not common and one atom which is common and a bonding distance between two atoms which are not common as an angle constraint condition designating a central angle formed by said three atoms with said common atom at its center, when two bonds each bonding two atoms have one common atom in the bond constraint list, and for releasing a constraint of an angle formed by three atoms by canceling the number of three atoms whose angle is constrained, with regard to a part of angle in the angle constraint list in accordance with a designation by a user;

torsion constraint condition setting and releasing means (100) for setting a torsion constraint list comprising a torsion constraint condition designating a combination of the numbers of four atoms comprising two atoms which are not common and two atoms which are common and a bonding distance between two atoms which are not common, when two groups each comprising three atoms for forming an angle have two common atoms in the angle constraint list, as a torsion constraint condition for designating an angle formed by two planes including two atoms which are not common and an intersection line which bonds two common atoms, and for releasing a constraint of a torsion formed by four atoms by canceling the number of four atoms whose torsion is constrained with regard to at least a part of torsion in the torsion constraint list in accordance with a designation by a user; and means for using the torsion constraint condition in a molecular dynamics simulator to simulate a behavior of the molecule.

* * * * *